United States Patent [19]

Perricone

[11] Patent Number: 5,122,536
[45] Date of Patent: Jun. 16, 1992

[54] METHOD FOR THE TOPICAL TREATMENT OF PSORIASIS

[76] Inventor: Nicholas V. Perricone, 350 Cosey Beach Ave., East Haven, Conn. 06512

[21] Appl. No.: 420,284

[22] Filed: Oct. 12, 1989

[51] Int. Cl.⁵ .................... A61K 31/34; A61K 31/185
[52] U.S. Cl. .............................. 514/474; 424/DIG. 5; 514/863; 514/937; 514/944
[58] Field of Search ............................. 514/863, 474; 424/DIG. 5

[56] References Cited

FOREIGN PATENT DOCUMENTS 1000724  3/1989  Belgium ............................. 514/863

OTHER PUBLICATIONS

Calarasu, Apr. 1989, vol. 110, 141559r Chemical Abstracts.
Komazaki et al., 1987, vol. 106, 38247f.

Primary Examiner—Dale R. Ore
Attorney, Agent, or Firm—St. Onge Steward Johnston & Reens

[57] ABSTRACT

A method for the therapeutic treatment of psoriasis in which acsorbic acid, or a precursor or derivative thereof, is topically applied to the affected skin areas.

10 Claims, No Drawings

METHOD FOR THE TOPICAL TREATMENT OF PSORIASIS

BACKGROUND OF THE INVENTION

The present invention relates to the skin disease known as psoriasis and, more particularly, to compositions and methods for the treatment of psoriasis.

Psoriasis is a chronic, recurrent, scaling skin disease of unknown etiology. Erythematous eruptions, often in papules or plaques, and usually having a white, silvery scale, can affect any part of the skin, but most commonly affect the scalp, the extensor surfaces of the elbows and knees, and the lower portion of the back. The disease usually occurs in adults, but children may also be affected. Over one million people in the United States have the discomfort and disfigurement of psoriasis, and of these more than 11% have experienced disability of such severity as to compromise employment and effectiveness. Patients with psoriasis have a much greater incidence of arthritis, and generalized exfoliation and even death can threaten afflicted individuals.

Psoriasis is without cure, and the course and remission of the disease are unpredictable, even capricious. Current therapeutic regimens include topical or intralesional application of corticosteroids, topical administration of anthralin or keratolytics, and use of tar and UV light on affected areas. These many treatments all have their benefits and drawbacks, and many factors must be considered in the choice of therapy. No single therapy is ideal, and it is rare for a patient not to be treated with several alternatives during the relapsing and remitting course of the disease. Whereas systematic treatment can induce prompt resolution of psoriatic lesions, suppression often requires ever-increasing doses, sometimes with toxic side effects, and tapering of therapy may result in rebound phenomena with extensions of lesions, possibly to exfoliation.

Information representing the current state of the art with respect to psoriasis and its treatment can be found in, e.g., Lowe, Nicholas J., Practical Psoriasis Therapy, Year Book Medical Publishers, Chicago, 1986, pp. 11-13; Mier, Paul D., and van de Kerhof, Peter C. M., eds., Textbook of Psoriasis, Churchill Livingstone, New York, 1986, pp. 13-39, 167 et seq; and Wyngaarden, James B., and Smith, Lloyd H., Cecil's Textbook of Medicine, W. B. Saunders Co., Philadelphia, 1988, pp. 2326-2327.

The primary object of this invention is to provide a treatment for psoriasis, and more particularly, to provide a therapy based upon topical application to affected skin areas of an active agent or precursor thereof, preferably in association with a dermatologically acceptable carrier or vehicle.

SUMMARY OF THE INVENTION

In accordance with the present invention, a therapeutic method for the treatment of psoriasis is provided which comprises topical application to the affected sites of the disease of an effective amount of ascorbic acid or an ascorbic acid precursor or derivative.

In the preferred practice of the invention, the ascorbic acid (or precursor or derivative) is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas.

As used herein, the terminology "ascorbic acid or an ascorbic acid precursor or derivative" is intended to embrace ascorbic acid per se, compounds (precursors) which upon topical application to the skin release or are converted to ascorbic acid per se, and compounds (derivatives), such as the salts, esters or anhydrides of ascorbic acid which either release or are converted to ascorbic acid upon topical application in accordance with the invention or which otherwise provide to the skin the effective ascorbic acid functionality.

The amount of the ascorbic acid or precursor or derivative thereof (hereinafter referred to collectively as ascorbic acid for ease of reference) necessary to bring about the therapeutic treatment of psoriasis is not fixed per se, and necessarily is dependent upon the severity and extent of the disease, the form of the ascorbic acid employed, and the concentration of the ascorbic acid when employed in association with a carrier. Generally, the ascorbic acid or composition containing it is topically applied to the affected skin areas in a predetermined or as-needed regimen (e.g., twice daily) to bring about improvement (e.g., thinning of plaques, decrease in scaling, decreased erythema), it generally being the case that gradual improvement is noted with each successive application. Insofar as has been determined based upon clinical studies to date, no adverse side effects are encountered.

DETAILED DESCRIPTION OF THE INVENTION

Ascorbic acid (vitamin C) and many of its precursors and derivatives are solid compounds at ambient conditions, having varying degrees of solubility in water, organic solvents, oils and the like. Since topical application to affected sites of psoriasis according to the invention requires that the active ingredient be in a form permitting such use, it generally will be the case that the ascorbic acid or precursor or derivative thereof be employed in association with a carrier, and particularly one in which the active ingredient is soluble per se or is effectively solubilized (e.g., as an emulsion or microemulsion). It is necessary that the carrier be inert in the sense of not bringing about a deactivation of the ascorbic acid or precursor or derivative, and in the sense of not bringing about any adverse effect on the skin areas to which it is applied.

Suitable carriers include water, alcohols, oils and the like, chosen for their ability to dissolve or disperse the active ingredient at concentrations of active ingredient most suitable for use in the therapeutic treatment. Generally, even low concentrations of active ingredient in a carrier will be suitable, requiring only that more frequent topical application be resorted to. As a practical matter, however, to avoid the need for repeated application, it is desirable that the topically applied composition (i.e., ascorbic acid or precursor or derivative plus carrier) be formulated to contain at least about 0.5% by weight, more preferably at least about 2% by weight, and most preferably at least about 10% by weight, of the active ingredient, and accordingly, carriers will be chosen which can solubilize or disperse the active ingredient at such concentrations.

While the carrier for the ascorbic acid or precursor or derivative of ascorbic acid can consist of a relatively simple solvent or dispersant such as water or oils, it is generally preferred that the carrier comprise a composition more conducive to topical application, and particularly one which will form a film or layer on the skin to which it is applied so as to localize the application and provide some resistance to washing off by immersion in water or by perspiration and/or aid in percutaneous delivery of the active ingredient. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

As noted, the ascorbic acid is provided in the form of the acid per se or in the form of a precursor or derivative. Exemplary compounds include the simple ionic salts (e.g., sodium ascorbate, calcium ascorbate, potassium ascorbate, magnesium ascorbate), fatty acid esters (e.g., ascorbyl palmitate, ascorbyl laurate, ascorbyl myristate, ascorbyl stearate), anhydrides, or other chemical derivatives or precursors which preserve or provide the effective acid compound upon dissolution or dispersion in a carrier or upon topical application. The most preferred compounds are the fatty acid esters of ascorbic acid, particularly ascorbyl palmitate. The fatsolubility of these compounds is such as to substantially aid in percutaneous delivery to lipid-rich layers in the affected skin areas, and also enables the active agent to be easily solubilized in fat-based carriers which further aid in penetration of skin layers. In addition, since ascorbic acid is rapidly oxidized in air, utilization of the fatty acid ester forms thereof, either alone or with a suitable carrier, enables the provision of stable preparations having a long shelf-life and prolonged effectiveness after topical application.

Yet further enhancement of the skin penetrability of the ascorbic acid can be obtained by applying the ascorbic acid (or precursor or derivative), or composition containing the ascorbic acid (or precursor or derivative), under occlusion, i.e., wherein there is applied over the topically applied compound or composition a dressing of the type known to enhance the penetration response of the skin to active compounds. One example of dressings of this type is the Actiderm self-adhesive patch available from Squibb & Co.

In a clinical program designed to test the effectiveness of the present invention, a composition was prepared consisting of 75 weight percent lecithin and 25 weight percent ascorbyl palmitate.

Twelve patients were examined in the study, five women and seven men, ranging in age from 19 to 71 years. All patients had psoriasis vulgaris plaque type varying in severity, and all had been using topical steroids for over six months with minimal benefit. The previously-described composition was applied to selected plaques once daily under occlusion using the earlier-mentioned Actiderm dressing, while other selected plaques were treated at the same time intervals with lecithin alone, also under occlusion with Actiderm dressing. The patients were examined at weekly intervals and assessed for clinical improvement. While some degree of improvement (seen as a thinning of plaques, and decrease in scaling and erythema) was noted for the areas treated with the control composition, dramatically better improvement was noted for the areas treated with the ascorbyl palmitate-containing composition. The average improvement over a period of two weeks of therapy was 60% for the ascorbyl palmitate-containing composition.

The mechanism of action of the therapeutic effectiveness of ascorbic acid for psoriasis is not known, although it is possible to postulate a theory, recognizing that the invention is not to be limited by the possible theory of mechanism. The biochemical events leading to the cutaneous inflammation in psoriasis have not been elucidated, but recent research has implicated metabolites of arachidonic acid in the pathogenesis of the disease. [Mier, et al., supra at 145, 171-172; Kragballe, Knud, and Voorhees, John J., Acta Dermatovener (Stockh) Suppl. 120, 12-17 (1986); Ruzicka, Thomas, Simmet, Thomas, Peskar, Bernhard A., and Rind, Johannes, J. Invest. Derm. 86, 105-108 (1986).] Arachidonic acid from esterified phospholipid sources in the cell can be released when phospholipases are triggered by a variety of hormones (directly or indirectly), by inflammatory or immunological stimuli, by calcium ionophores, by ultraviolet light, by melittin (the membrane active component of bee venom), by tumor promoting agents and even by mechanical agitation. [Kuehl, Frederick A., and Egan, Robert W., Science 210, 978-984 (1980).] The activity of phospholipase is, in fact, abnormally high in the whole epidermis of the psoriatic patient. [Mier et al., supra at 135.] After cleavage, free arachidonic acid is then enzymatically oxidized to yield potent biological agents by three major pathways. [Wyngaarden, et al., supra at 1271-1275.] The predominant two of these oxidative pathways produce substances with diverse properties and rapid metabolism; some of these compounds have been implicated in a range of physiologic processes and diverse human diseases, including bronchial asthma, inflammation, and unstable coronary disease. In the first pathway, a cyclooxygenase oxygentates arachidonic acid to an endoperoxide intermediate, which is then converted to a variety of other biologically active compounds including an array of classical prostaglandins. By an alternate route, a lipoxygenase oxidizes arachidonic acid (IUPAC name, 5,6,11,14-eicosatetraenoic acid) to hydroperoxyeicosatetraenoic acids (known as HPETEs) which are converted to hydroeicosatetraenoic acids (HETEs) and leukotrienes.

Several lines of evidence suggest that products of the lipoxygenase pathway may have a role in the pathogenesis of psoriasis: 1) benoxaprofen, a potent lipoxygenase inhibitor, improves psoriasis; 2) indomethacin, a potent inhibitor of cyclooxygenase, worsens psoriasis; 3) extremely high levels of HETEs as well as arachidonic acid are found in keratome slices of psoriatic skin lesions, whereas only modest increase in prostaglandins have been reported; 4) leukotrienes can be recovered from abraded psoriatic skin lesions; and 5) the topical application of leukotriene to skin or the infusion of HETE into skin results in intraepidermal microabscesses morphologically similar to early psoriatic events. [Kragballe et al., supra at 13-14.]

The most effective topical treatment for psoriasis is currently corticosteroids. Whereas the complex mechanism of action of this class of drugs is not understood, corticosteroids are known to result in phospholipase inhibition. It has been postulated that increased levels of corticosteroids suppress arachidonic acid release, and thus the biosynthesis of pathological inflammatory mediators, HETEs and leukotrienes. [Mier, supra, at 145.]

The use of ascorbic acid in the treatment of asthma and investigation of human lung parenchyma in vitro has shown that ascorbate increases quantities of prostaglandins in human lung tissue. [Fann, Y.D., et al., Prostaglandins 31:361-365 (1986); Parker, C. and Snider, D., Prostaglandins and Asthma, Ann. Int. Med. 78:963-65 (1973); Mushinin, V., Effect of Ascorbic Acid on Response to Methacholine Challenge in Asthmatic Subjects, Am. Rev. Respir. Dis. 127:143-47 (1983)]. Low vitamin C reserves had been noted in association with asthma, and earlier studies had suggested that ascorbate may be capable of modulating prostaglandin formation generally. [Counsell, J.N., and Hornig, D.H., Vitamin C (Ascorbic Acid), Applied Science Publishers, New Jersey, 1981, pp. 14, 36.] Studies using ascorbic acid to enhance production of prostaglandins and decrease the severity of airway constriction have implicated a role of the acid in the enhancement of the cyclooxygenase pathway. [Fann, et al., supra; Parker and Snider, supra; Mushinin, supra; Ogilvy, C.S., et al., J. Allergy Clin. Immunol. 67:363-69 (1981)]. When indomethacin, a cyclooxygenase inhibitor, was administered to asthmatic subjects concurrently with ascorbic acid therapy, there was no decrease in airway constriction like that observed when ascorbic acid was used alone. And low concentrations of other reducing agents (epinephrine, phenol, and hydroquinone) stimulate cyclooxygenase in vitro, probably by protecting against oxidative deactivation. [Kuehl, et al., p. 982.]

It is possible, then, that the noted effectiveness of the ascorbic acid treatment of psoriasis might at least in part be due to the activity of ascorbic acid, as a reducing agent, in stimulating cyclooxygenase activity in epidermal cells in a manner analogous to the postulated mechanism of action of ascorbic acid in lung tissue. For this reason, it would appear that the useful derivatives or precursors of ascorbic acid are those which either release or convert to ascorbic acid per se or, at the least, preserve the reducing agent activity of ascorbic acid.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims.

What is claimed is:

1. A method for the treatment of psoriasis, said treatment comprising topically applying to the affected skin areas an effective amount of a composition consisting essentially of at least about 10% by weight of a compound selected from the group consisting of calcium salt of ascorbic acid, magnesium salt of ascorbic acid, esters of ascorbic acid, anhydrides of ascorbic acid, and mixtures thereof.

2. A method for the treatment of psoriasis, said treatment comprising topically applying to the affected skin areas an effective amount of a composition consisting essentially of a compound selected from the group consisting of calcium salt of ascorbic acid, magnesium salt of ascorbic acid, esters of ascorbic acid, anhydrides of ascorbic acid, and mixtures thereof.

3. A method according to claim 2 wherein said compound is a fatty acid ester of ascorbic acid or a mixture of fatty acid esters of ascorbic acid.

4. A method according to claim 3 wherein said compound is ascorbyl palmitate.

5. A method according to claim 1 wherein said composition further comprises a dermatologically acceptable carrier.

6. A method according to claim 5 wherein said composition is in a form selected from the group consisting of solution, dispersion, cream, lotion, gel or solid stick.

7. A method for the treatment of psoriasis, said treatment comprising topically applying to the affected skin areas an effective amount of a composition consisting essentially of ascorbyl palmitate in associaition with a dermatologically acceptable carrier.

8. A method for the treatment of psoriasis, said method comprising topically applying to the affected skin areas an effective amount of a composition comprising a fatty acid ester of ascorbic acid.

9. A method to claim 8 wherein said fatty acid ester of ascorbic acid is present in said composition in an amount of at least about 2% by weight of said composition.

10. A method according to claim 9 wherein said fatty acid ester of ascorbic acid is ascorbyl palmitate.

* * * * *